(12) United States Patent
Jeong et al.

(10) Patent No.: US 8,058,007 B2
(45) Date of Patent: Nov. 15, 2011

(54) CYCLIC REVERSE TRANSCRIPTION METHOD

(75) Inventors: Hui Jeong Jeong, Daejeon (KR); Min-Jung Kim, Seoul (KR); Hae-Joon Park, Gyeonggi-do (KR); Han Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 62 days.

(21) Appl. No.: 12/531,778

(22) PCT Filed: Mar. 19, 2008

(86) PCT No.: PCT/KR2008/001545
§ 371 (c)(1), (2), (4) Date: Sep. 17, 2009

(87) PCT Pub. No.: WO2008/115002
PCT Pub. Date: Sep. 25, 2008

(65) Prior Publication Data
US 2010/0221786 A1    Sep. 2, 2010

(30) Foreign Application Priority Data
Mar. 19, 2007 (KR) .................. 10-2007-0026846

(51) Int. Cl.
*C12Q 1/68* (2006.01)
*C12P 19/34* (2006.01)

(52) U.S. Cl. ............... 435/6.12; 435/91.1; 435/91.2

(58) Field of Classification Search ......... 435/6, 91.1, 435/91.2
See application file for complete search history.

(56) References Cited

U.S. PATENT DOCUMENTS

| | | | |
|---|---|---|---|
| 5,194,596 A | * | 3/1993 | Tischer et al. ............ 530/399 |
| 5,834,254 A | | 11/1998 | Shen et al. |
| 5,858,702 A | * | 1/1999 | Agre ..................... 435/69.1 |
| 6,261,770 B1 | * | 7/2001 | Warthoe .................... 435/6 |
| 6,271,004 B1 | * | 8/2001 | Warthoe ................. 435/91.51 |
| 6,406,891 B1 | | 6/2002 | Legerski |

FOREIGN PATENT DOCUMENTS
KR    1998-702110    7/1998

OTHER PUBLICATIONS

Y. Mizuno et al., "Increased specificity of reverse transcription priming by trehalose and oligo-blockers allows high-efficiency window separation of mRNA display", *Nucleic Acids Research* 1999, vol. 27, No. 5, pp. 1345-1349.

P. Carninci et al., "Thermostabilization and thermoactivation of thermolabile enzymes by trehalose and its application for the synthesis of full length cDNA", *Proc. Natl. Acad. Sci. USA* Jan. 1998, vol. 95, pp. 520-524.

A. Spiess et al., "A Highly Efficient Method for Long-Chain cDNA Synthesis Using Trehalose and Betaine", *Analytical Biochemistry* 2002, vol. 301, pp. 168-174.

L. Chen et al., "Trehalose as a good candidate for enriching full-length cDNAs in cDNA library construction", *Journal of Biotechnology* 2007, vol. 127, pp. 402-407.

* cited by examiner

*Primary Examiner* — Kenneth R. Horlick
(74) *Attorney, Agent, or Firm* — Clark & Brody (57) ABSTRACT

Disclosed is a cyclic reverse transcription method, which comprises performing reverse transcription reaction in one or more cycles, each cycle comprising the steps of: (i) performing reaction with a reverse transcription reaction solution comprising template RNA, RNA-dependent DNA polymerase, a reaction buffer, primers for reverse transcription and dNTPs, and optionally, a stabilizer, at 10° C. to 40° C. and, (ii) performing reaction with the resultant reaction solution at 42° to 55° C.

15 Claims, 3 Drawing Sheets

```
                       SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: Forward primer for transferrin receptor gene

<400> SEQUENCE: 1
gtggcgtata gtaaggctgc aacagttact                              30

<210> SEQ ID NO 2
<211> LENGTH: 30
<212> TYPE: DNA
<213> ORGANISM: Artificial Sequence
```

```
<220> FEATURE:
<223> OTHER INFORMATION: Reverse primer for transferrin receptor gene

<400> SEQUENCE: 2
tgctggtacc aagaaccgct ttatccagat                                    30

<210> SEQ ID NO 3
<211> LENGTH: 26
<212> TYPE: DNA
<213> ORGANISM: Artificial Sequence
<220> FEATURE:
<223> OTHER INFORMATION: Forward primer for transferrin receptor gene

<400> SEQUENCE: 3
gtggcagttc agaatgatgg atcaag                                        26

<210> SEQ ID NO 4
<211> LENGTH: 25
<212> TYPE: DNA
<213> ORGANISM: Artificial Sequence
<220> FEATURE:
<223> OTHER INFORMATION: Reverse primer for transferrin receptor gene

<400> SEQUENCE: 4
accacttaca accttcagca gagac                                         25

<210> SEQ ID NO 5
<211> LENGTH: 20
<212> TYPE: DNA
<213> ORGANISM: Artificial Sequence
<220> FEATURE:
<223> OTHER INFORMATION: Forward primer for GAPDH gene

<400> SEQUENCE: 5
ggaaggtgaa ggtcggagtc                                               20

<210> SEQ ID NO 6
<211> LENGTH: 22
<212> TYPE: DNA
<213> ORGANISM: Artificial Sequence
<220> FEATURE:
<223> OTHER INFORMATION: Reverse primer for GAPDH gene

<400> SEQUENCE: 6
cctgttcctg tagccaaatt cg                                            22

<210> SEQ ID NO 7
<211> LENGTH: 22
<212> TYPE: DNA
<213> ORGANISM: Artificial Sequence
<220> FEATURE:
<223> OTHER INFORMATION: Forward primer for b-actin gene

<400> SEQUENCE: 7
gaagagctac gagctgcctg ac                                            22

<210> SEQ ID NO 8
<211> LENGTH: 22
<212> TYPE: DNA
<213> ORGANISM: Artificial Sequence
<220> FEATURE:
<223> OTHER INFORMATION: Reverse primer for b-actin gene

<400> SEQUENCE: 8
gagtacttgc gctcaggagg ag                                            22
```

```
<210> SEQ ID NO 9
<211> LENGTH: 20
<212> TYPE: DNA
<213> ORGANISM: Artificial Sequence
<220> FEATURE:
<223> OTHER INFORMATION: Forward primer for ELAVL1 gene

<400> SEQUENCE: 9
tttgttctgg ttggggttgg                                              20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for ELAVL1 gene

<400> SEQUENCE: 10
cccgcatcca gatttttgaa                                              20
```

CYCLIC REVERSE TRANSCRIPTION METHOD

TECHNICAL FIELD

The present invention relates to a cyclic reverse transcription method, and more specifically, to the cyclic reverse transcription method, which comprises performing reverse transcription reaction in one or more cycles, each cycle comprising the steps of performing reaction with a reverse transcription reaction solution comprising template RNA, RNA-dependent DNA polymerase, a reaction buffer, primers for reverse transcription and dNTPs, and optionally, a stabilizer, at 10° C. to 40° C., and performing reaction with the resultant reaction solution at 42° C. to 55° C., to maximize the efficiency and improve the sensitivity of the reaction.

BACKGROUND ART

Analysis of mRNA is very important to understand various biological phenomena. Based on the founding of RNA-dependent DNA polymerase, i.e., reverse transcriptase, in retroviruses, synthesis of cDNA from template RNA (total RNA and mRNA), i.e., reverse transcription, is now possible. This is one of basic tools for genetic study and one of essential key techniques applied in various fields including molecular biology, biology, pharmaceuticals, forensic medicine, viral diagnosis, and the like.

In the conventional reverse transcription method, cDNA is synthesized at a relatively low temperature of 37° C. to 42° C. As a result, the template forms the secondary structure, which interrupts cDNA synthesis during reverse transcription reaction. To overcome this problem, a method using a thermophilic reverse transcriptase has been proposed. However, primers for reverse transcription have a short length, that is, random primers have the length of 5mer to 15mer and dT primers have the length of 14mer to 23mer. Therefore, at a high temperature, the primers could not be fully annealed with the template, resulting in decrease in the reaction efficiency.

DISCLOSURE

Technical Problem

To maximize the efficiency of reverse transcription reaction, the present inventors contemplated a cyclic reverse transcription method, which comprises performing reverse transcription reaction in one or more cycles, each cycle comprising the steps of performing reaction for a given time at a temperature to make the annealing of primer with template RNA feasible, and then, performing reaction for a given time at another temperature to make the secondary structure of template RNA resolved and reverse transcription reaction feasible, while the reaction is performed at a constant temperature in the conventional method. As the conventional Moloney Murine Leukemia Virus (MMLV) reverse transcriptase could not react at a high temperature, the present invention employs a stabilizer enabling the reaction at 50° C. to 55° C., to resolve the secondary structure of template RNA. When a stabilizer is not employed, the reaction with the reverse transcriptase could be performed at 42° C. to lower than 50° C.

Therefore, it is an object of the present invention to provide a method to maximize the efficiency and increase the sensitivity of the reaction, by overcoming the problems of the conventional reverse transcription method to synthesize cDNA from template RNA.

Technical Solution

To achieve the above object, one aspect of the present invention provides a cyclic reverse transcription method, which comprises performing reverse transcription reaction in one or more cycles, each cycle comprising the steps of:

(i) performing reaction with a reverse transcription reaction solution comprising template RNA, RNA-dependent DNA polymerase, a reaction buffer, primers for reverse transcription and dNTPs at 10° C. to 40° C. (hereinafter, sometimes referred to as the 'step of 10° C. to 40° C.'); and, (ii) performing reaction with the resultant reaction solution at 42° C. to 55° C. (hereinafter, sometimes referred to as the 'step of 42° C. to 55° C.').

Another aspect of the present invention provides a reverse transcription polymerase chain reaction (RT-PCR) method, comprising the steps of:

(i) synthesizing cDNA according to the above-described cyclic reverse transcription method; and, (ii) performing polymerase chain reaction (PCR) using the synthesized cDNA as template.

DESCRIPTION OF DRAWINGS

The above and other objects, features and advantages of the present invention will become apparent from the following description of preferred embodiments given in conjunction with the accompanying drawings, in which.

BEST MODE

Hereinafter, the present invention will be described in detail.

Generally, reverse transcription polymerase chain reaction (RT-PCR) consists of the following two steps; converting RNA extracted from a sample into cDNA and amplifying the cDNA with DNA polymerase. The present invention makes it possible to maximize the efficiency of converting RNA into cDNA. That is, in the present invention, the reverse transcription reaction is performed at 10° C. to 40° C. to ensure good accessibility of primers to the template, and then, at 50° C. to 55° C. wherein the conventional RNA-dependent DNA polymerase could not have reacted, in the presence of a stabilizer, or at 42° C. to lower than 50° C. wherein the RNA-dependent DNA polymerase could react even in the absence of a stabilizer, to resolve the secondary structure of template RNA, thereby to increase the conversion efficiency of RNA into cDNA.

In the present invention, the reverse transcription reaction solution can be prepared as an aqueous solution containing template RNA, RNA-dependent DNA polymerase, a reaction buffer, primers for reverse transcription and dNTPs, and optionally, a stabilizer. As an alternative, the reverse transcription reaction solution can be prepared by mixing RNA dependent DNA polymerase, a reaction buffer, primers for reverse transcription and dNTPs, and optionally, a stabilizer, drying the mixture, adding template RNA thereto, and rehydrating the resultant mixture. Or, it can be prepared by mixing RNA dependent DNA polymerase, a reaction buffer and dNTPs, and optionally, a stabilizer, drying the mixture, adding template RNA and primers for reverse transcription thereto, and rehydrating the resultant mixture. At this time, if necessary, a stabilizer can be additionally added to the dried mixture before rehydration. Further, for the convenience in use depending upon the purpose of use, other components than one or more specific ones among the RNA dependent DNA polymerase, the reaction buffer, the stabilizer and the dNTPs can be mixed and dried, and then, the specific one(s) can be added thereto, followed by rehydration. For example, to adjust the concentration of each component, e.g., Tris-HCl, KCl, $MgCl_2$ or DTT, of the reaction buffer to optimize the reaction, or to select a specific component and determine its optimal concentration to improve the reactivity, other components than the reaction buffer, that is, RNA dependent DNA polymerase and dNTPs (or RNA dependent DNA polymerase, dNTPs and primers for reverse transcription), and optionally, a stabilizer are mixed and dried, and then, template RNA, the reaction buffer and primers for reverse transcription (or template RNA and the reaction buffer) are added to the dried mixture, followed by rehydration, thereby to perform the reaction more easily and conveniently. At this time, if necessary, a stabilizer can be additionally added to the dried mixture before rehydration. Otherwise, in case of adjusting the concentration of RNA dependent DNA polymerase or determining an appropriate amount of concentrated and purified RNA dependent DNA polymerase to increase reactivity, other components than the RNA dependent DNA polymerase, that is, a reaction buffer and dNTPs (or a reaction buffer, dNTPs and primers for reverse transcription), and optionally, a stabilizer are mixed and dried first, and then, template RNA, the RNA dependent DNA polymerase and primers for reverse transcription (or template RNA and the RNA dependent DNA polymerase) are added thereto, followed by rehydration, thereby to perform the reaction more easily and conveniently. At this time, if necessary, a stabilizer can be additionally added to the dried mixture before rehydration.

The stabilizer that can be used in this invention is not specially limited. For example, in case that the reverse transcription reaction solution is prepared as an aqueous solution, the stabilizer can be selected from the group consisting of trehalose, dimethyl sulfoxide (DMSO), betaine, bovine serum albumin (BSA) and a mixture thereof, but is not limited thereto. In case that the reverse transcription reaction solution is prepared by rehydrating the dried mixture, the stabilizer can be selected from the group consisting of monosaccharides, disaccharides, polysaccharide, carbohydrate derivatives and a mixture thereof. Monosaccharides include triose, tetrose, pentose, hexose, heptose, etc. The pentose is exemplified by arabinose, xylose, ribose, xylulose, and ligrose. The hexose is exemplified by galactose, glucose, mannose, sorbose, and fructose, but not limited thereto. Disaccharides include trehalose, xylobiose, maltose, isomaltose, laminaribiose, cellobiose, gentiobiose, lactose, and sucrose. Carbohydrate derivatives include arabitol, xylitol, galactitol, sorbitol, mannitol, and methyl glucopyranoside, but are not limited thereto. Among them, a mixture of trehalose and other stabilizer is preferred.

In the cyclic reverse transcription method of the present invention, in case of using a stabilizer, the step of 42° C. to 55° C. preferably comprises performing the reaction at 50° C. to 55° C. It is more preferred to perform the reaction in 1 cycle to 20 cycles, particularly, 2 cycles to 20 cycles, each cycle consisting of performing the reaction at 10° C. to 40° C. for 10 seconds to 5 minutes, and then, at 50° C. to 55° C. for 10 seconds to 5 minutes. This is because the conversion efficiency of template RNA into cDNA, and ultimately, the yield of DNA are increased with the above duration and number of cycles.

A random primer or dT primer is generally used for reverse transcription reaction. Preferably, the random primer has the length of about 5mer to 15mer, and the dT primer has the length of about 14mer to 23mer. For instance, the random primer is randomly synthesized without pre-determined nucleotide sequence, G, A, T or C, and thus, in case of random timer, an oligomer having only one kind nucleotide, e.g., an oligomer with 6 Ts or 6 Gs, might be synthesized. Oligomers with 6 Ts and 6 Gs have annealing temperatures of about 12° C. and about 24° C., respectively, which are different by at least 10° C. Random primers have annealing temperatures as various as their combinations of nucleotide sequences. According to the conventional reaction performed at a constant temperature, in case of using primers for reverse transcription having a lower annealing temperature than the reaction temperature or various annealing temperatures, the reaction efficiency cannot but be decreased. In the present invention, by involving the step of performing annealing reaction at 10° C. to 40° C., even primers having a lower annealing temperature than the reaction temperature or various annealing temperatures can be fully annealed, thereby to maximize the reaction efficiency.

In case of using a stabilizer, the step of 42° C. to 55° C. is preferably performed sequentially at 42° C. to lower than 50° C., and then, at 50° C. to 55° C., to further increase the conversion efficiency of RNA into cDNA. This is because the RNA dependent DNA polymerase is not genetically thermophilic, even though it has somewhat increased thermo-stability in the presence of a stabilizer, and so the reverse transcription reaction is preferably performed at 42° C. to lower than 50° C. as an intermediate step, rather than be directly performed at the high temperature. In this case, the reaction is performed in 1 cycle to 20 cycles, each cycle consisting of reaction at 10° C. to 40° C. for 10 seconds to 5 minutes, reaction at 42° C. to lower than 50° C. for 10 seconds to 5 minutes, and reaction at 50° C. to 55° C. for 10 seconds to 5 minutes.

When a stabilizer is not used, it is preferable that the step of 10° C. to 40° C. is performed at 10° C. to 25 t, and the step of 42° C. to 55° C. is performed at 42° C. to lower than 50° C. In this case, the reaction is performed in 1 cycle to 20 cycles, each cycle consisting of reaction at 10° C. to 25° C. for 10 seconds to 5 minutes, and reaction at 42° C. to lower than 50° C. for 10 seconds to 5 minutes.

The temperature range of the present invention has been arbitrarily determined considering the general reaction temperature of the conventional RNA dependent DNA polymerase of around 42° C. The temperature and its duration are not specially limited, but can be modified as long as they meet the purpose of the present invention, which would be obvious to ones skilled in the art.

Herein, the term, 'template RNA,' refers to RNA to be amplified into DNA, including total RNA or mRNA extracted from a sample.

The term, 'RNA dependent DNA polymerase,' refers to reverse transcriptase, including ones originated from Avian Myeloblastosis Virus (AMV), Moloney Murine Leukemia Virus (MMLV) and Human Immunodeficiency Virus (HIV). Particularly, in this invention, a stabilizer is added so that the MMLV reverse transcriptase that could not have reacted at 50° C. to 55° C. can react at that temperature, to maximize the efficiency and increase the sensitivity of the reaction. If a stabilizer is not added, the reverse transcription reaction is preferably performed at 42° C. to lower than 50° C.

The reaction buffer is preferably any of conventional buffers appropriate for the RNA dependent DNA polymerase. In particular, the reaction buffer for MMLV reverse transcriptase can be selected from the group consisting of Tris-HCl, $MgCl_2$, DTT (dithiothreitol) and KCl, but is not limited thereto. Depending upon the purpose of the present invention, any reaction buffer can be used as long as it does not affect the activity and the stability of RNA dependent DNA polymerase.

Practical and presently preferred embodiments of the present invention are illustrative as shown in the following Examples. However, it will be appreciated that those skilled in the art, on consideration of this disclosure, may make modifications and improvements within the spirit and scope of the present invention.

EXAMPLE 1

Amplification of Transferrin Receptor Gene of Various Lengths

A random 12mer (400 pmoles/20 µl reaction solution), MMLV reverse transcriptase (Bioneer; 800 U/20 µl reaction solution), 10× reaction buffer (2 µl), RNasin (Promega; 15 U/20 µl reaction solution), trehalose (Fluka; 400 mM/20 µl reaction solution), α-MG (methyl-α-D-glucopyranoside) (Sigma; 200 mM/20 µl reaction solution) and dNTPs (25 mM/20 µl reaction solution) were pre-mixed as 2× solution, and the solution was distributed in SnapStrip 8-strip PCR Tubes (SSI) by 10 µl. The solution was dried in a vacuum drier (CENTRA Evaporator™; Bioneer) at room temperature for 80 minutes to obtain the dried reverse transcription reaction mixture containing the random primer on the bottom of the tube. Another dried reverse transcription reaction mixture containing dT 20mer (Bioneer; 70 pmoles/20 µl reaction solution) was prepared according to the same manner as described above.

900 ng of total RNA extracted and purified from HeLa cells by using AccuPrep Tissue RNA Prepmate (Bioneer) was added to the dried reverse transcription reaction mixtures each containing the random primer and dT primer. Then, distilled water treated with 0.1% DEPC (diethylpyrocarbonate) was added thereto to rehydrate the mixture to a total volume of 20 µl, to prepare the reverse transcription reaction solution. Reverse transcription reaction was performed with the prepared reverse transcription reaction solution at 42° C. for 30 minutes and 55° C. for 30 minutes, respectively, according to the conventional method; and, in 6 cycles, each cycle consisting of reaction at 37° C. for 2 minutes and reaction at 50° C. for 3 minutes, and in 6 cycles, each cycle consisting of reaction at 37° C. for 1 minute, 47° C. for 3 minutes and 55° C. for 1 minute, respectively, according to the present invention. Then, PCR was performed with 3 j of the cDNA synthesized according to the above reverse transcription reaction as template to amplify the transferrin receptor gene of various lengths (800 bp, 1.5 kb, 2.0 kb and 2.6 kb). The sequences of primers used for the PCR were as follows.

①800 bp
F:
(SEQ. ID. NO: 1)
5'-GTG GCG TAT AGT AAG GCT GCA ACA GTT ACT-3',

R:
(SEQ. ID. NO: 2)
5'-TGC TGG TAC CAA GAA CCG CTT TAT CCA GAT-3';

②1.5 kb
F:
(SEQ. ID. NO: 3)
5'-GTG GCA GTT CAG AAT GAT GGA TCA AG-3',

R:
(SEQ. ID. NO: 2)
5'-TGC TGG TAC CAA GAA CCG CTT TAT CCA GAT-3';

-continued

③ 2.0 kb
F:
(SEQ. ID. NO: 1)
5'-GTG GCG TAT AGT AAG GCT GCA ACA GTT ACT 3',

R:
(SEQ. ID. NO: 4)
5'-ACC ACT TAC AAC CTT CAG CAG AGA C-3'

④ 2.6 kb
F:
(SEQ. ID. NO: 3)
5'-GTG GCA GTT CAG AAT GAT GGA TCA AG-3',

R:
(SEQ. ID. NO: 4)
5'-ACC ACT TAC AAC CTT CAG CAG AGA C-3'.

PCR was performed as follows; denaturation at 94° C. for 5 minutes, 40 cycles of denaturation at 94° C. for 40 seconds, annealing at 60° C. for 40 seconds and extension at 72° C. for 90 seconds, followed by final extension at 72° C. for 5 minutes.

Figure 1:
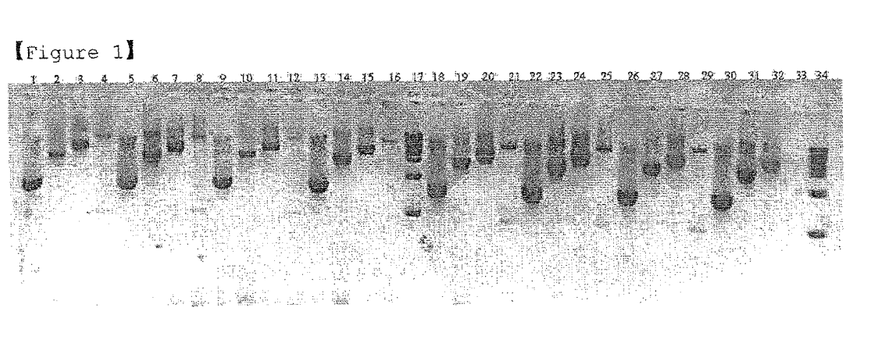
FIG. 1 is a photograph showing the result of electrophoresis for amplified transferrin receptor gene of various lengths. Primers, MMLV reverse transcriptase, 10× reaction buffer, a stabilizer and dNTPs were pre-mixed as 2× solution, and the solution was distributed, dried and rehydrated to prepare the reverse transcription reaction solution. Template RNA (total RNA extracted from HeLa cells) was added to the above reaction solution, followed by performing reverse transcription at a constant temperature and at cyclic temperatures, respectively. The transferrin receptor gene was amplified and confirmed by electrophoresis.

The results are shown in FIG. 1. As shown in FIG. 1, in both cases of using random primer and dT primer, the cyclic reverse transcription showed higher amplification rate and sensitivity than the conventional method performed at a constant temperature. Even in case of the long target, the cyclic reverse transcription showed higher amplification rate and sensitivity than the conventional method performed at a constant temperature. Table 1 provides the description of FIG. 1.

EXAMPLE 2

Amplification of GAPDH and β-actin After Cyclic Reverse Transcription with dT Primer and Various Concentrations of Template RNA The reverse transcription reaction mixture was prepared according to substantially the same manner as described in Example 1, except using dT primer (Bioneer; 70 pmoles/20 μl reaction solution) and various concentrations (100 ng, 10 ng, 1 ng and 100 pg) of total RNA extracted and purified from HeLa cells. Reverse transcription reaction was performed with the reverse transcription reaction solution at 42° C. for 1 hour and 55° C. for 1 hour, respectively, according to the conventional method; and, in 12 cycles, each cycle consisting of reaction at 37° C. for 2 minutes and reaction at 50° C. for 3 minutes, and cycles, each cycle consisting of reaction at 37° C. for 1 minute, reaction at 47° C. for 3 minutes and reaction at 55° C. for 1 minute, respectively, according to the present invention. 2 μl of the synthesized cDNA was taken and used as template for PCR. The sequences of 1 kb GAPDH primer and 300 by β-actin primer were as follows.

TABLE 1

| | Lane number | | | | | | | |
|---|---|---|---|---|---|---|---|---|
| | lane 1 | lane 2 | lane 3 | lane 4 | lane 5 | lane 6 | lane 7 | lane 8 |
| Reaction condition | 42° C. for 30 minutes | | | | | | | |
| Primer | | dT20 | | | | random 12mer | | |
| Gene length (bp) | 800 | 1500 | 2000 | 2600 | 800 | 1500 | 2000 | 2600 |
| | Lane number | | | | | | | |
| | lane 9 | lane 10 | lane 11 | lane 12 | lane 13 | lane 14 | lane 15 | lane 16 |
| Reaction condition | 55° C. for 30 minutes | | | | | | | |
| Primer | | dT20 | | | | random 12mer | | |
| Gene length (bp) | 800 | 1500 | 2000 | 2600 | 800 | 1500 | 2000 | 2600 |
| | Lane number | | | | | | | |
| | lane 18 | lane 19 | lane 20 | lane 21 | lane 22 | lane 23 | lane 24 | lane 25 |
| Reaction condition | 37° C. for 2 minutes, 50° C. for 3 minutes, 6 cycles | | | | | | | |
| Primer | | dT20 | | | | random 12mer | | |
| Gene length (bp) | 800 | 1500 | 2000 | 2600 | 800 | 1500 | 2000 | 2600 |
| | Lane number | | | | | | | |
| | lane 26 | lane 27 | lane 28 | lane 29 | lane 30 | lane 31 | lane 32 | lane 33 |
| Reaction condition | 37° C. for 1 minute, 47° C. for 3 minutes, 55° C. for 1 minute, 6 cycles | | | | | | | |
| Primer | | dT20 | | | | random 12mer | | |
| Gene length (bp) | 800 | 1500 | 2000 | 2600 | 800 | 1500 | 2000 | 2600 |

(Lanes 17 and 34: 1 kb marker)

① 1 kb GAPDH
F:
(SEQ. ID. NO: 5)
5'-GGA AGG TGA AGG TCG GAG TC-3',

R:
(SEQ. ID. NO: 6)
5'-CCT GTT CCT GTA GCC AAA TTC G-3';

② 300 bp β-actin
F:
(SEQ. ID. NO: 7)
5'-GAA GAG CTA CGA GCT GCC TGA C-3',

R:
(SEQ. ID. NO: 8)
5'-GAG TAC TTG CGC TCA GGA GGA G-3'.

PCR was performed as follows; denaturation at 94° C. for 5 minutes, 35 cycles of denaturation at 94° C. for 40 seconds, annealing at 57° C. for 40 seconds and extension at 72° C. for 1 minute, followed by final extension at 72° C. for 5 minutes.

Figure 2:
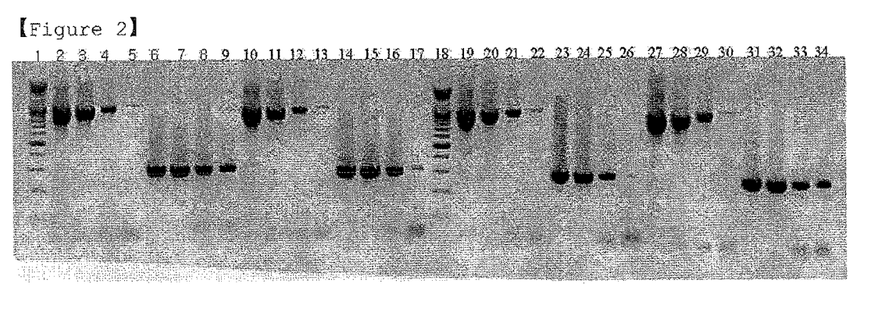
FIG. 2 is a photograph showing the result of electrophoresis for amplified GAPDH and β-actin genes. Primers, MMLV reverse transcriptase, 10× reaction buffer, a stabilizer and dNTPs were pre-mixed as 2× solution, and the solution was distributed, dried and rehydrated to prepare the reverse transcription reaction solution. Template RNA was added to the above reaction solution, followed by performing reverse transcription at a constant temperature and at cyclic temperatures, respectively. The GAPDH and β-actin genes were amplified and confirmed by electrophoresis.

The results are shown in FIG. 2. As shown in FIG. 2, the cyclic reverse transcription method was proved more efficient than the conventional method performed at a constant temperature. Table 2 provides the description of FIG. 2.

TABLE 2

| | Lane number | | | | | | | |
|---|---|---|---|---|---|---|---|---|
| | lane 2 | lane 3 | lane 4 | lane 5 | lane 6 | lane 7 | lane 8 | lane 9 |
| Reaction condition | 42° C. for 1 hour | | | | | | | |
| Primer for reverse transcription | dT20 | | | | | | | |
| Amount of template RNA (ng) | 100 | 10 | 1 | 0.1 | 100 | 10 | 1 | 0.1 |
| PCR primer | GAPDH primer | | | | β-actin primer | | | |

| | Lane number | | | | | | | |
|---|---|---|---|---|---|---|---|---|
| | lane 10 | lane 11 | lane 12 | lane 13 | lane 14 | lane 15 | lane 16 | lane 17 |
| Reaction condition | 55° C. for 1 hour | | | | | | | |
| Primer for reverse transcription | dT20 | | | | | | | |
| Amount of template RNA (ng) | 100 | 10 | 1 | 0.1 | 100 | 10 | 1 | 0.1 |
| PCR primer | GAPDH primer | | | | β-actin primer | | | |

| | Lane number | | | | | | | |
|---|---|---|---|---|---|---|---|---|
| | lane 19 | lane 20 | lane 21 | lane 22 | lane 23 | lane 24 | lane 25 | lane 26 |
| Reaction condition | 37° C. for 2 minutes, 50° C. for 3 minutes, 12 cycles | | | | | | | |
| Primer for reverse transcription | dT20 | | | | | | | |
| Amount of template RNA (ng) | 100 | 10 | 1 | 0.1 | 100 | 10 | 1 | 0.1 |
| PCR primer | GAPDH primer | | | | β-actin primer | | | |

| | Lane number | | | | | | | |
|---|---|---|---|---|---|---|---|---|
| | lane 27 | lane 28 | lane 29 | lane 30 | lane 31 | lane 32 | lane 33 | lane 34 |
| Reaction condition | 37° C. for 1 minute, 47° C. for 3 minutes, 55° C. for 1 minute, 12 cycles | | | | | | | |
| Primer for reverse transcription | dT20 | | | | | | | |
| Amount of template RNA (ng) | 100 | 10 | 1 | 0.1 | 100 | 10 | 1 | 0.1 |
| PCR primer | GAPDH primer | | | | β-actin primer | | | |

(Lanes 1 and 18: 100 bp marker)

EXAMPLE 3

Amplification of GAPDH and β-actin Gene After Cyclic Reverse Transcription with a Random Primer and Various Concentrations of Template RNA The reverse transcription reaction solution was prepared according to substantially the same manner as described in Example 1, except using a random primer (Bioneer; 400 pmoles/20 μl reaction mixture) and various concentrations (100 ng, 10 ng, 1 ng and 100 pg) of total RNA extracted and purified from HeLa cells. Reverse transcription reaction was performed with the reverse transcription reaction solution at 42° C. for 1 hour and 55° C. for 1 hour, respectively, according to the conventional method; and, in 12 cycles, each cycle consisting of reaction at 37° C. for 2 minutes and reaction at 42° C. for 3 minutes, and 12 cycles, each cycle consisting of reaction at 37° C. for 1 minute, reaction at 47° C. for 3 minutes and reaction at 55° C. for 1 minute, respectively, according to the present invention. 2 μl of the synthesized cDNA was taken and used as template for PCR. The sequences of 1 kb GAPDH primer and 300 by β-actin primer were as described in Example 2.

PCR was performed as follows; denaturation at 94° C. for 5 minutes, 35 cycles of denaturation at 94° C. for 40 seconds, annealing at 57° C. for 40 seconds and extension at 72° C. for 1 minute, followed by final extension at 72° C. for 5 minutes.

Figure 3:
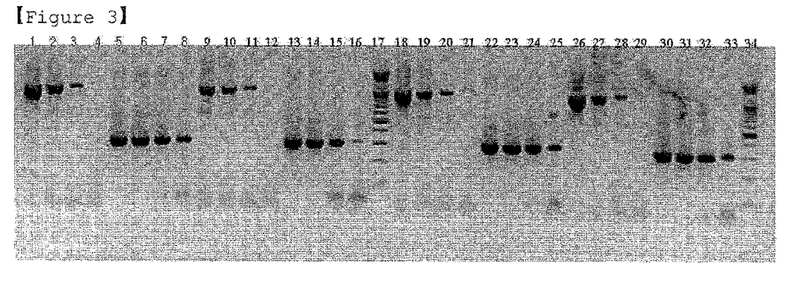
FIG. 3 is a photograph showing the result of electrophoresis for amplified GAPDH and β-actin genes. Primers, MMLV reverse transcriptase, 10× reaction buffer, a stabilizer and dNTPs were pre-mixed as 2× solution, and the solution was distributed, dried and rehydrated to prepare the reverse transcription reaction solution. Template RNA was added to the above reaction solution, followed by performing reverse transcription at a constant temperature and at cyclic temperatures, respectively. The GAPDH and β-actin genes were amplified and confirmed by electrophoresis.

The results are shown in FIG. 3. As shown in FIG. 3, the cyclic reverse transcription method was proved more efficient than the conventional method performed at a constant temperature. Table 3 provides the description of FIG. 3.

TABLE 3

| | Lane number | | | | | | | |
|---|---|---|---|---|---|---|---|---|
| | lane 1 | lane 2 | lane 3 | lane 4 | lane 5 | lane 6 | lane 7 | lane 8 |
| Reaction condition | | | | 42° C. for 1 hour | | | | |
| Primer for reverse transcription | | | | random 12mer | | | | |
| Amount of template RNA (ng) | 100 | 10 | 1 | 0.1 | 100 | 10 | 1 | 0.1 |
| PCR primer | | GAPDH primer | | | | β-actin primer | | |

| | Lane number | | | | | | | |
|---|---|---|---|---|---|---|---|---|
| | lane 9 | lane 10 | lane 11 | lane 12 | lane 13 | lane 14 | lane 15 | lane 16 |
| Reaction condition | | | | 55° C. for 1 hour | | | | |
| Primer for reverse transcription | | | | random 12mer | | | | |
| Amount of template RNA (ng) | 100 | 10 | 1 | 0.1 | 100 | 10 | 1 | 0.1 |
| PCR primer | | GAPDH primer | | | | β-actin primer | | |

| | Lane number | | | | | | | |
|---|---|---|---|---|---|---|---|---|
| | lane 18 | lane 19 | lane 20 | lane 21 | lane 22 | lane 23 | lane 24 | lane 25 |
| Reaction condition | | | | 37° C. for 2 minutes, 50° C. for 3 minutes, 12 cycles | | | | |
| Primer for reverse transcription | | | | random 12mer | | | | |
| Amount of template RNA (ng) | 100 | 10 | 1 | 0.1 | 100 | 10 | 1 | 0.1 |
| PCR primer | | GAPDH primer | | | | β-actin primer | | |

| | Lane number | | | | | | | |
|---|---|---|---|---|---|---|---|---|
| | lane 26 | lane 27 | lane 28 | lane 29 | lane 30 | lane 31 | lane 32 | lane 33 |
| Reaction condition | | | | 37° C. for 1 minute, 47° C. for 3 minutes, 55° C. for 1 minute, 12 cycles | | | | |
| Primer for reverse transcription | | | | random 12mer | | | | |
| Amount of template RNA (ng) | 100 | 10 | 1 | 0.1 | 100 | 10 | 1 | 0.1 |
| PCR primer | | GAPDH primer | | | | β-actin primer | | |

(Lanes 17 and 34: 100 bp marker)

EXAMPLE 4

Amplification of 5'-terminal 600 by of 6 kb Human ELAVL1 Gene After Cyclic Reverse Transcription with dT 20 Primer and Template RNA with Various Reaction Times The reverse transcription reaction solution was prepared by mixing 10 ng of total RNA extracted and purified, dT20 primer (Bioneer; 100 pmoles/20 µl reaction solution), MMLV reverse transcriptase (Bioneer; 200 U/20 µl reaction solution), 0 of 10× reaction buffer, RNasin (Promega; 15 U/20 µl reaction solution) and betaine (Sigma; 500 mM/20 µl reaction solution), according to the same manner as described in Example 1. Reverse transcription reaction was performed with the prepared reverse transcription reaction solution at 42° C. and 52° C. for 10, 20, 40, and 60 minutes, respectively, according to the conventional methods; and in 2, 4, 8 and 12 cycles, each cycle consisting of reaction at 37° C. for 2 minutes and reaction at 50° C. for 3 minutes, and 2, 4, 8 and 12 cycles, each cycle consisting of reaction at 37° C. for 1 minute, reaction at 47° C. for 3 minutes and reaction at 55° C. for 1 minute, respectively, according to the present invention. 4 µl of the synthesized cDNA was taken and used as template for PCR. The sequences of ELAVL1 primers were as follows.

```
Human ELAVL1
F:
5'-TTT GTT CTG GTT GGG GTT GG-3'   (SEQ. ID. NO: 9)

R:
5'-CCC GCA TCC AGA TTT TTG AA-3'   (SEQ. ID. NO: 10)
```

PCR was performed as follows: denaturation at 94° C. for 5 minutes, 40 cycles of denaturation at 94° C. for 1 minute, annealing at 57° C. for 1 minute and extension at 72° C. for 1 minute, followed by final extension at 72° C. for 5 minutes.

Figure 4:
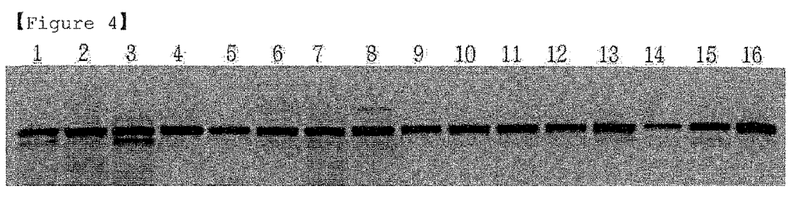
FIG. 4 is a photograph showing the result of electrophoresis for amplified ELAVL1 gene. Reverse transcription was performed with the reverse transcription reaction solution comprising template RNA, primers, MMLV reverse transcriptase, 10× reaction buffer, a stabilizer and dNTPs at a constant temperature and at cyclic temperatures, respectively. The ELAVL1 gene was amplified and confirmed by electrophoresis.

The results are shown in FIG. 4. As shown in FIG. 4, the cyclic reverse transcription method showed less non-specific PCR bands and larger amount of amplification, than the conventional method performed at a constant temperature, in the synthesis of long human cDNA such as ELAVL1 cDNA. Table 4 provides the description of FIG. 4.

EXAMPLE 5

Amplification of Human GAPDH Gene After Cyclic Reverse Transcription with dT 20 Primer and Template RNA with Different Reaction Times The reverse transcription reaction solution was prepared by mixing 10 ng of total RNA extracted and purified, dT20 primer (Bioneer; 100 pmoles/20 µl reaction solution), MMLV reverse transcriptase (Bioneer; 200 U/20 µl reaction solution), 2 µl of 10× reaction buffer, RNasin (Promega; 15 U/20 reaction solution) and betaine (Sigma; 500 mM/20 µl reaction solution), according to the same manner as described in Example 1. Reverse transcription reaction was performed with the prepared reverse transcription reaction solution at 42° C. for 10, 20, 40, and 60 minutes, respectively, according to the conventional method; and in 1, 2, 4 and 6 cycles, each cycle consisting of reaction at 37° C. for 30 seconds, reaction at 42° C. for 4 minutes, reaction at 47° C. for 5 minutes and reaction at 55° C. for 30 seconds, respectively, according to the present invention. 2 µl of the synthesized cDNA was used as template for PCR, and PCR was performed with the template and human GAPDH primer set. PCR was performed as follows; denaturation at 94° C. for 5 minutes, 25 cycles of denaturation at 94° C. for 40 seconds, annealing at 57° C. for 40 seconds and extension at 72° C. for 1 minute, followed by final extension at 72° C. for 5 minutes. The sequences of GAPDH primers were as shown in Example 2.

Figure 5:
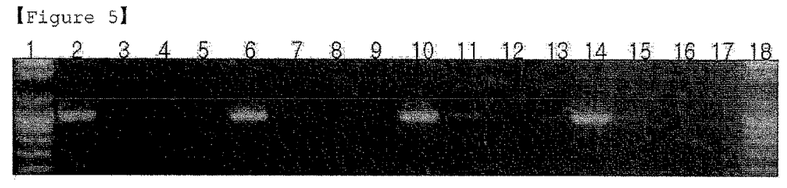
FIGS. 5 and 6 are photographs showing the result of electrophoresis for amplified GADPH gene. Reverse transcriptions were performed with the reverse transcription reaction solution comprising template RNA, dT20 primers, MMLV reverse transcriptase, 10× reaction buffer, a stabilizer and dNTPs, at a constant temperature and at cyclic temperatures, respectively. The GADPH gene was amplified and confirmed by electrophoresis.
Figure 6:
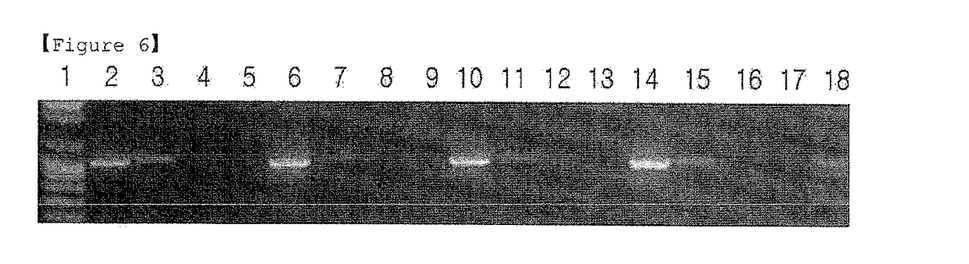

The results are shown in FIGS. 5 and 6. As shown in FIGS. 5 and 6, the cyclic reverse transcription showed higher amplification rate even with shorter reaction time and smaller amount of template RNA than the conventional method performed at 42° C. for 1 hour. Table 5 provides the description of FIG. 5, and Table 6 provides the description of FIG. 6.

TABLE 4

|  | Lane number | | | | | | | |
| --- | --- | --- | --- | --- | --- | --- | --- | --- |
|  | lane 1 | lane 2 | lane 3 | lane 4 | lane 5 | lane 6 | lane 7 | lane 8 |
| Reaction temperature (° C.) |  | 42 | | |  | 52 | | |
| Reaction time (min) | 10 | 20 | 40 | 60 | 10 | 20 | 40 | 60 |

|  | Lane number | | | | | | | |
| --- | --- | --- | --- | --- | --- | --- | --- | --- |
|  | lane 9 | lane 10 | lane 11 | lane 12 | lane 13 | lane 14 | lane 15 | lane 16 |
| Reaction condition |  | 37° C. for 2 minutes, 50° C. for 3 minutes | | |  | 37° C. for 1 minute, 47° C. for 3 minutes, 55° C. for 1 minute | | |
| No. of cycles | 2 | 4 | 8 | 12 | 2 | 4 | 8 | 12 |

TABLE 5

| | Lane number | | | | | | | |
|---|---|---|---|---|---|---|---|---|
| | lane 2 | lane 3 | lane 4 | lane 5 | lane 6 | lane 7 | lane 8 | lane 9 |
| Reaction temperature (° C.) | | | | 42 | | | | |
| Reaction time (min) | | 10 | | | | 20 | | |
| Reaction time (min) | 10 | 1 | 0.1 | 0.01 | 10 | 1 | 0.1 | 0.01 |

| | Lane number | | | | | | | |
|---|---|---|---|---|---|---|---|---|
| | lane 10 | lane 11 | lane 12 | lane 13 | lane 14 | lane 15 | lane 16 | lane 17 |
| Reaction temperature (° C.) | | | | 42 | | | | |
| Reaction time (min) | | 40 | | | | 60 | | |
| Reaction time (min) | 10 | 1 | 0.1 | 0.01 | 10 | 1 | 0.1 | 0.01 |

(Lanes 1 and 18: 100 bp marker)

TABLE 6

| | Lane number | | | | | | | |
|---|---|---|---|---|---|---|---|---|
| | lane 2 | lane 3 | lane 4 | lane 5 | lane 6 | lane 7 | lane 8 | lane 9 |
| Reaction condition | 37° C. for 30 seconds, 42° C. for 4 minutes, 47° C. for 5 minutes, 55° C. for 30 seconds | | | | | | | |
| No. of cycles | | 1 | | | | 2 | | |
| Amount of template RNA (ng) | 10 | 1 | 0.1 | 0.01 | 10 | 1 | 0.1 | 0.01 |

| | Lane number | | | | | | | |
|---|---|---|---|---|---|---|---|---|
| | lane 10 | lane 11 | lane 12 | lane 13 | lane 14 | lane 15 | lane 16 | lane 17 |
| Reaction condition | 37° C. for 30 seconds, 42° C. for 4 minutes, 47° C. for 5 minutes, 55° C. for 30 seconds | | | | | | | |
| No. of cycles | | 4 | | | | 6 | | |
| Amount of template RNA (ng) | 10 | 1 | 0.1 | 0.01 | 10 | 1 | 0.1 | 0.01 |

(Lanes 1 and 18: 100 bp marker)

EXAMPLE 6

Amplification of Human GAPDH Gene After Reverse Transcription with Random 6mer, Random 9mer and dT15 Primer and the Template RNA with Various Reaction Times MMLV reverse transcriptase (Bioneer; 200 U/20 µl reaction solution), 10× reaction buffer (2 µl), RNasin (Promega; 15 U/20 µl reaction solution) and dNTPs (25 mM/20 µl reaction solution) were pre-mixed as 2× solution, and the solution was distributed in SnapStrip 8-strip PCR Tubes (SSI) by 10 µl. The solution was dried in a vacuum drier (CENTRA Evaporator™; Bioneer) at room temperature for 80 minutes to obtain the dried reverse transcription reaction mixture on the bottom of the tube. Random timer, random 9mer and dT15 primer (Bioneer; random primer 200 pmoles/20 µl reaction mixture, dT15 primer 100 pmole/20 µl reaction mixture) were used as primers for the reverse transcription. The total RNA extracted and purified from HeLa cells was diluted to 100 ng, 10 ng, 1 ng and 100 pg, as template. The template was added to the dried reverse transcription reaction mixture, and the resultant mixture was rehydrated to prepare the reverse transcription reaction solution. Reverse transcription reaction was performed with the rehydrated reverse transcription reaction solution at 42° C. for 1 hour, according to the conventional method; and in 12 cycles, each cycle consisting of reaction at 12° C. for 1 minute and reaction at 42° C. for 4 minutes, according to the present invention. 2 µl of the synthesized cDNA was used as template for PCR. The sequences of 1 kb GAPDH primer were as shown in Example 2.

PCR was performed as follows; denaturation at 94° C. for 5 minutes, 35 cycles of denaturation at 94° C. for 40 seconds, annealing at 57° C. for 40 seconds and extension at 72° C. for 1 minute, followed by final extension at 72° C. for 5 minutes.

Figure 7:
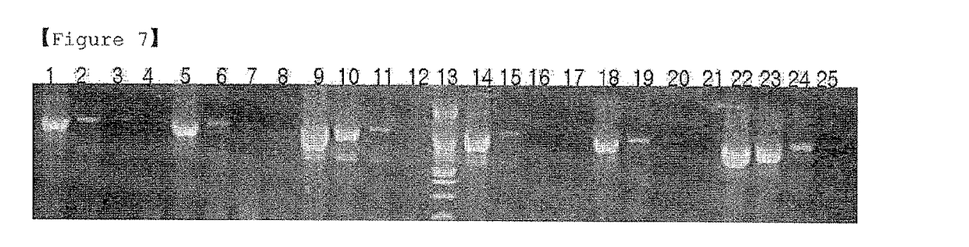
FIG. 7 is a photograph showing the result of electrophoresis for amplified GADPH gene. MMLV reverse transcriptase, 10× reaction buffer and dNTPs were pre-mixed as 2× solution, and the solution was distributed, dried and rehydrated to prepare the reverse transcription reaction solution. Primers for reverse transcription and template RNA were added to the above reaction solution, followed by performing reverse transcription at a constant temperature and at cyclic temperatures, respectively. The GAPDH gene was amplified and confirmed by electrophoresis.

The results are shown in FIG. 7. As shown in FIG. 7, the cyclic reverse transcription method was proved more efficient than the conventional method performed at a constant temperature. Table 7 provides the description of FIG. 7.

TABLE 7

| | Lane 1 | Lane 2 | Lane 3 | Lane 4 | Lane 5 | Lane 6 | Lane 7 | Lane 8 | Lane 9 | Lane 10 | Lane 11 | Lane 12 |
|---|---|---|---|---|---|---|---|---|---|---|---|---|
| Reaction condition | 42° C. for 1 hour | | | | | | | | | | | |
| Primer for reverse transcription | random 6mer | | | | random 9mer | | | | dT15 | | | |
| Amount of template RNA (ng) | 100 | 10 | 1 | 0.1 | 100 | 10 | 1 | 0.1 | 100 | 10 | 1 | 0.1 |
| PCR primer | GAPDH primer | | | | | | | | | | | |

| | Lane 14 | Lane 15 | Lane 16 | Lane 17 | Lane 18 | Lane 19 | Lane 20 | Lane 21 | Lane 22 | Lane 23 | Lane 24 | Lane 25 |
|---|---|---|---|---|---|---|---|---|---|---|---|---|
| Reaction condition | 12° C. for 1 minute, 42° C. for 4 minutes, 12 cycles | | | | | | | | | | | |
| Primer for reverse transcription | random 6mer | | | | random 9mer | | | | dT15 | | | |
| Amount of template RNA (ng) | 100 | 10 | 1 | 0.1 | 100 | 10 | 1 | 0.1 | 100 | 10 | 1 | 0.1 |
| PCR primer | GAPDH primer | | | | | | | | | | | |

(Lane 13: 100 bp marker)

INDUSTRIAL APPLICABILITY

As described above, while the conventional reverse transcription method is performed at a constant temperature, the cyclic reverse transcription method comprises performing reverse transcription reaction in one or more cycles, each cycle comprising reaction at a temperature to make primers be fully annealed with template RNA, and reaction at a temperature to resolve the secondary structure of template RNA and make reverse transcriptase react, thereby to maximize the reaction efficiency resulting in increase in amplification rate and sensitivity.

[Sequence Listing Free Text]

SEQ ID No. 1 is the nucleotide sequence of forward primer for amplification of transferrin receptor gene (800 by and 2.0 kb);

SEQ ID No. 2 is the nucleotide sequence of reverse primer for amplification of transferrin receptor gene (800 by and 1.5 kb);

SEQ ID No. 3 is the nucleotide sequence of forward primer for amplification of transferrin receptor gene (1.5 kb and 2.6 kb);

SEQ ID No. 4 is the nucleotide sequence of reverse primer for amplification of transferrin receptor gene (2.0 kb and 2.6 kb);

SEQ ID No. 5 is the nucleotide sequence of forward primer for amplification of GADPH gene (1 kb);

SEQ ID No. 6 is the nucleotide sequence of reverse primer for amplification of GADPH gene (1 kb);

SEQ ID No. 7 is the nucleotide sequence of forward primer for amplification of β-actin gene (300 bp);

SEQ ID No. 8 is the nucleotide sequence of reverse primer for amplification of β-actin gene (300 bp);

SEQ ID No. 9 is the nucleotide sequence of forward primer for amplification of human ELAVL1 gene); and SEQ ID No. 10 is the nucleotide sequence of reverse primer for amplification of human ELAVL1 gene.

The invention claimed is:

1. A cyclic reverse transcription method, which comprises performing reverse transcription reaction in two or more cycles, each cycle comprising the steps of:
   (i) performing reaction with a reverse transcription reaction solution comprising template RNA, RNA-dependent DNA polymerase, a reaction buffer, primers for reverse transcription and dNTPs at 10° C. to 40° C.; and,
   (ii) performing reaction with the resultant reaction solution at 42° C. to 55° C.

2. The cyclic reverse transcription method according to claim 1, wherein the reverse transcription reaction solution further comprises a stabilizer, and in step (ii), the reaction is performed at 50° C. to 55° C.

3. The cyclic reverse transcription method according to claim 2, wherein the reaction is performed in 2 to 20 cycles, each cycle comprising reaction at 10° C. to 40° C. for 10 seconds to 5 minutes, and reaction at 50° C. to 55° C. for 10 seconds to 5 minutes.

4. The cyclic reverse transcription method according to claim 2, wherein the reaction is performed sequentially at 42° C. to lower than 50° C., and then, at 50° C. to 55° C. in step (ii).

5. The cyclic reverse transcription method according to claim 4, wherein the reaction is performed in 2 to 20 cycles, each cycle comprising reaction at 10° C. to 40° C. for 10 seconds to 5 minutes, reaction at 42° C. to lower than 50° C. for 10 seconds to 5 minutes, and reaction at 50° C. to 55° C. for 10 seconds to 5 minutes.

6. The cyclic reverse transcription method according to claim 1, wherein in step (i), the reaction is performed at 10° C. to 25° C., and in step (ii), the reaction is performed at 42° C. to lower than 50° C.

7. The cyclic reverse transcription method according to claim 6, wherein the reaction is performed in 2 to 20 cycles, each cycle comprising reaction at 10° C. to 25° C. for 10 seconds to 5 minutes, and reaction at 42° C. to lower than 50° C. for 10 seconds to 5 minutes.

8. The cyclic reverse transcription method according to claim 1, wherein the RNA dependent DNA polymerase is Moloney Murine Leukemia Virus (MMLV) reverse transcriptase.

9. The cyclic reverse transcription method according to claim 1, wherein the primers for reverse transcription are random primers of 5mer to 15mer or dT primers of 14mer to 23mer.

10. The cyclic reverse transcription method according to claim 1, wherein the reverse transcription reaction solution is prepared as an aqueous solution.

11. The cyclic reverse transcription method according to claim 10, wherein the reverse transcription reaction solution further comprises a stabilizer selected from the group consisting of trehalose, dimethyl sulfoxide, betaine, bovine serum albumin and/or a mixture thereof.

12. The cyclic reverse transcription method according to claim 1, wherein the reverse transcription reaction solution is prepared by mixing the components excluding template RNA, drying the mixture, adding template RNA and a stabilizer thereto, and rehydrating the resultant mixture.

13. The cyclic reverse transcription method according to claim 1, wherein the reverse transcription reaction solution is prepared by mixing the components excluding template RNA and an additional component selected from the group consisting of RNA dependent DNA polymerase, a reaction buffer, primers for reverse transcription, dNTPs and a mixture thereof, drying the mixture, adding the excluded components and a stabilizer thereto, and rehydrating the resultant mixture.

14. The cyclic reverse transcription method according to claim 2, wherein the stabilizer comprises trehalose.

15. A reverse transcription polymerase chain reaction method, comprising the steps of:
   (i) synthesizing cDNA according to the cyclic reverse transcription method of claim 1; and,
   (ii) performing polymerase chain reaction (PCR) using the synthesized cDNA as template.

* * * * *